United States Patent [19]

Laine

[11] Patent Number: 5,914,239
[45] Date of Patent: Jun. 22, 1999

[54] DIAGNOSIS OF FUNGAL INFECTIONS, AND A CHITIN-BINDING LECTIN USEFUL IN SUCH DIAGNOSES

[75] Inventor: Roger A. Laine, Baton Rouge, La.

[73] Assignee: Board of Supervisors of Louisiana State University and Agricultural and Mechanical College, Baton Rouge, La.

[21] Appl. No.: 08/745,881

[22] Filed: Nov. 8, 1996

Related U.S. Application Data

[60] Provisional application No. 60/035,112, Nov. 15, 1995.

[51] Int. Cl.$^6$ .................................................. G01N 33/53
[52] U.S. Cl. ........................... 435/7.31; 435/7.9; 435/34; 435/35; 436/518
[58] Field of Search .................. 435/7.31, 7.9, 435/34, 35, 968; 436/518

[56] References Cited

U.S. PATENT DOCUMENTS

| | | | |
|---|---|---|---|
| 5,004,699 | 4/1991 | Winters | 435/7.31 |
| 5,352,607 | 10/1994 | Laine et al. | 435/252.33 |
| 5,587,292 | 12/1996 | Laine . | |

FOREIGN PATENT DOCUMENTS

WO 92/17786   10/1992   WIPO .

OTHER PUBLICATIONS

Sasmal et al., N–Acetyl–D–glucosamine–specific lectin purified from *Vibrio cholerae* 01. FEMS Microbiology Letters 98:217–224, 1992.

Chamberland et al., "Chitinase–Gold Complex Used to Localize Chitin Ultrastructurally in Tomato Root Cells," Histochem. J., vol. 17, pp. 313–321 (1985).

Benhamou, et al., "Attempted Localization of a Substrate for Chitinases in Plant Cells Reveals Abundant N–acetyl–D–glucosamine Residues in Secondary Walls," Biology of the Cell, vol. 67, pp. 341–350 (1989).

M.A. Benjaminson, "Conjugates of Chitinase with Fluorescein Isothiocyanate or Lissamine Rhodamine as Specific Stains for Chitin In Situ," Stain Technology, vol. 44, pp. 27–31 (1969).

M.A. Benjaminson et al., "Ferritin–labelled Enzyme: a Tool for Electron Microscopy," Nature, vol. 210, pp. 1275–1276 (1966).

C. Yu et al., "The Sugar–Specific Adhesion/Deadhesion Apparatus of the Marine Bacterium *Vibrio furissii* is a Sensorium that Continuously Monitors Nutrient Levels in the Environment," Biochem. Biophys. Res. Commun., vol. 149, pp. 86–92 (1987).

C. Yu et al., "Chitin Utilization by Marine Bacteria," J. Biol. Chem., vol. 266, pp. 24260–24267 (1991).

M. Chrispeels et al., "Lectins, Lectin Genes, and Their Role in Plant Defense," Plant Cell, vol. 3, pp. 1–9 (1991).

J. Huesing et al., "Effect of Wheat Germ Isolectins on Development of Copea Weevil," Phytochemistry, vol. 30, pp. 785–788 (1991).

Van Parijs et al., "Hevein: An Antifungal Protein from Rubber–tree (Hevea brasiliensis) Latex," Planta, vol. 183, pp. 258–264 (1991).

O. Gildemeister et al., "Chitovibrin: a chitin–binding lectin from *Vibrio parahemolyticus,*" Glycoconjugate Journal, vol. 11, pp. 518–526 (Dec. 1994).

W. Broekaert et al., "A Chitin–Binding Lectin from Stinging Nettle Rhizomes with Antifungal Properties," Science, vol. 245, pp. 1100–1102 (1989).

J. Huesing et al., "Rice and Stinging Nettle Lectins: Insecticidal Activity Similar to Wheat Germ Agglutinin," Phytochemistry, vol. 30, pp. 3565–3568 (1991).

G. Wagner et al., "Chitin in the Epidermal Cuticle of a Vertebrate (*Paralipophyrs trigloides*, Blenniidae, Telesotei)," Experentia, vol. 49, pp. 317–319 (1993).

*Primary Examiner*—Donna C. Wortman
*Attorney, Agent, or Firm*—John H. Runnels

[57] ABSTRACT

A 134 kDa, calcium-independent, chitin-binding lectin called chitovibrin is secreted by marine bacteria of the genus Vibrio. The secretion of chitovibrin is inducible by chitin or chitin-oligomers. Chitovibrin shows no apparent enzymatic activity, but has a strong affinity for chitin and for chito-oligomers dp9 and larger. The protein has an isoelectric pH of 3.6, shows thermal tolerance, binds chitin with an optimum at pH 6 and is active in 0–4 M NaCl. Chitovibrin is useful as a stain for fungi and other chitin-containing organisms. Chitovibrin may be used to detect the presence of chitin, particularly in diagnosing fungal infections in humans, animals, and plant materials. Fungal infections are a particular problem in immunocompromised hosts such as AIDS patients and bone marrow transplant patients, because they can cause opportunistic infections. The chitovibrin diagnostic method allows the convenient, broad spectrum diagnosis of fungal infections in tissue samples or in body fluids. Other, smaller polypeptide fragments of chitovibrin will exhibit similar chitin-binding properties, and could be used in coupling to detection systems.

19 Claims, No Drawings

SEQUENCE LISTING

```
(1) GENERAL INFORMATION:

(iii) NUMBER OF SEQUENCES: 1

(2) INFORMATION FOR SEQ ID NO:1:

(i) SEQUENCE CHARACTERISTICS:
          (A) LENGTH: 25 amino acids
          (B) TYPE: amino acid
          (C) STRANDEDNESS: single
          (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO:1:

Ala Val Asp Ala Ala Pro Leu Glu Val Tyr Asp Ser Asn Lys Val Tyr
1               5                   10                  15

Asn Gly Gly Asp Gln Val Gln His Glu
            20                  25
```

DIAGNOSIS OF FUNGAL INFECTIONS, AND A CHITIN-BINDING LECTIN USEFUL IN SUCH DIAGNOSES

The benefit of the Nov. 15, 1995 filing date of provisional application 60/035,112 is claimed under 35 U.S.C. § 119(e).

The development of this invention was partially funded by the Government under USDA/CSREES HATCH appropriation LAB02877, awarded by the Department of Agriculture. The Government may have certain rights in this invention.

This invention pertains to the diagnosis of fungal infections, particularly to the diagnosis of fungal infections with a novel chitin-binding lectin.

Fungal infections are a major health problem, particularly in immunocompromised patients such as those with acquired immune deficiency syndrome (AIDS) or patients receiving a bone marrow transplant. Several million people worldwide are currently infected with the human immunodeficiency virus (HIV), the retrovirus that causes AIDS. AIDS is characterized by a profound derangement in the immune system, leading to multiple opportunistic infections and otherwise rare neoplasms.

Opportunistic diseases are the predominant direct causes of morbidity and mortality in AIDS patients. The Centers for Disease Control and the World Health Organization recognized the following fungal infections as important "indicator" diseases in their 1988 definition of AIDS: candidosis of the esophagus, trachea, bronchi, or lungs; and meningeal cryptococcosis. In the presence of laboratory evidence of HIV infection, disseminated coccidioidomycosis and histoplasmosis are also considered indicative of AIDS. It has been estimated that 58–81% of all AIDS patients contract a fungal infection at some time during the course of an AIDS infection, and that 10–20% of AIDS deaths are a direct consequence of fungal infections. Major mycoses related to AIDS include candidosis, cryptococcosis (yeasts), histoplasmosis, and coccidioidomycosis (dimorphic fungi). Deep, severe, but relatively rare mycoses related to AIDS include penicilliosis, blastomycosis, paracoccidioidomycosis, sporotrichosis, aspergillosis, mucormycosis, various yeast infections, and nocardiosis. Cutaneous fungal infections related to AIDS include seborrheic dermatitis, dermatophytosis, trichosporonosis, and alternariosis.

Aspergillosis, although less common in AIDS patients, is a common fungal infection in other immunodepressed patients, such as bone marrow transplant patients, and can occur at a rate as high as 70% in patients with leukemia after 30 days of neutropenia.

In addition to the pathological damage directly caused by fungal infections, fungal antigens may also act as a T-cell suppressor cofactor in the development of AIDS. While small amounts of fungal antigen can stimulate the immune response, an excess of antigen may have an adverse effect on cell-mediated immunity. Circulating fungal antigens, such as mannan in candidosis, and glucuronoxylomannan in cryptococcosis, may be present in excess in acute fungal infections. Candidal antigens in particular may be important cofactors in AIDS. It is imperative that treatment be undertaken rapidly and efficiently before these conditions lead to invasive forms.

Despite their prevalence, systemic fungal infections are difficult to diagnose in living AIDS patients. Unfortunately, autopsy is often the only available route to diagnose fungal infections. AIDS patients with fungal infections may have nonspecific symptoms for long periods of time. It has been difficult to establish definitive diagnoses from patients' body fluids. Histologic identification of organisms requires invasive procedures, with possible attending complications. Isolation of the organisms in blood culture, when possible, can sometimes be used for diagnosis. Even so, proper diagnosis is delayed because of the time required to process the specimens and to culture the fungus. This delay alone can result in progressive deterioration. Some AIDS patients with fungal infections respond to appropriate therapy quickly with early diagnosis, although continued lifetime treatment may be necessary due to the abnormal underlying immune system, and the fact that current anti-fungal pharmaceuticals are fungistatic rather than fungicidal.

To improve the care of AIDS patients and other immunocompromised patients, there is an unfilled need for better means for early diagnoses of fungal infections. Prompt implementation of an appropriate antifungal therapy provides a better environment for antiviral chemotherapy. Despite recent advances in anti-fungal therapeutics that show promise in treating many mycoses, there is a continuing need for a rapid, sensitive, accurate, and broad-spectrum fungal diagnostic method.

There is also an unfilled need for better means to diagnose fungal infections in plant tissues, both in growing plants and in harvested crops and foods. Direct economic losses in agriculturally important crops caused by fungal infections cost billions of dollars annually.

Chitin is a class of polymers of N-acetyl-glucosamine (GlcNAc). Chitin and glucan, another polysaccharide, are the major constituents of the cell walls of most fungi.

Many currently available fungal diagnostic methods are designed to detect specific anti-fungal antibodies in body fluids such as blood or serum, for example, anti-*Candida albicans*, anti-Cryptococcus, anti-Histoplasma, anti-Blastomyces, anti-Aspergillus and anti-Coccidioidomyces. These antibody-detection tests include immunodiffusion, latex antibody agglutination, complement fixation, and ELISA.

Molecular Probes, Inc. markets a metabolic stain for live fungi; this stain is not useful, however, for staining fungi in fixed histology specimens.

Other methods are available for the selective histologic identification of fungal organisms in tissue specimens, but each of these methods has disadvantages. These methods generally have a broader sensitivity than the antibody detection methods, meaning that they can recognize more than one species of fungi. In addition to their individual disadvantages, a common disadvantage of most existing methods is that they are difficult to apply to samples of body fluids, because proper sample fixation can be difficult.

Grocott methenamine silver nitrate (GMS) staining is by far the most common currently used method in the pathology laboratory. GMS stains polysaccharides in most fungal organisms, creating a contrasting image between the fungus and the host tissue. The stain is not as effective when it is used in cytospin or other body fluid samples. GMS staining can be non-specific, due to its indiscriminate recognition of connective tissue polysaccharides (e.g., glycosaminoglycans and mucin).

Other histochemical stains for fungal organisms include calcofluor/cellufluor, India Ink, lectin label, and Rylus BSU.

Calcofluor/Cellufluor: This method uses calcofluor/cellufluor, which fluoresces under ultraviolet light, to bind to the chitin of fungal organisms. This method inherently relies on fluorescence microscopy, limiting its use in small clinics. Calcofluor/cellufluor is not specific to chitin, as it also labels several other polysaccharides, including cellulose fibers, which are common contaminants in skin samples.

India Ink: This method uses India Ink to detect capsulated organisms such as Cryptococci. The method is limited because many fungal cells lack such a capsule.

Lectin label: Lectins having chitin-binding properties (e.g., wheat germ agglutinin) have been used to stain fungi. However, interferences from non-specific staining of other carbohydrates have been a problem.

Rylus BSU: This method also involves staining the chitinous cell walls of fungal organisms with a substance that fluoresces under ultraviolet light. This method also inherently relies on fluorescence microscopy, limiting its use in small clinics.

Chamberland et al., "Chitinase-Gold Complex Used to Localize Chitin Ultrastructurally in Tomato Root Cells," Histochem. J., Vol. 17, pp 313–321 (1985) discusses the use of a fungal-extracted chitinase conjugated with gold to detect chitin in a *Fusarium oxysporum* infection of tomato root cells. Detection was performed with an electron microscope. See also Benhamou, et al., "Attempted Localization of a Substrate for Chitinases in Plant Cells Reveals Abundant N-acetyl-D-glucosamine Residues in Secondary Walls," Biology of the Cell, vol. 67, pp. 341–50 (1989).

M. A. Benjaminson, "Conjugates of Chitinase with Fluorescein Isothiocyanate or Lissamine Rhodamine as Specific Stains for Chitin In Situ," Stain Technology, vol. 44, pp. 27–31 (1969) discloses the use of a fluorescent-labelled chitinase as a stain for insect and fungus morphology.

M. A. Benjaminson et al., "Ferritin-labelled Enzyme: A Tool for Electron Microscopy," Nature, vol. 210, pp. 1275–1276 (1966) discloses the use of a ferritin-labelled chitinase to stain *Aspergillus niger*. Fluorescein isothiocyanate-labelled chitinase is also mentioned.

Co-pending, commonly-assigned patent application Ser. No. 08/402,772 discloses a method for diagnosing fungal infections with a chitinase. While this method is very useful for visualizing fungal organisms, some investigators have expressed a concern (not shared by the present inventor) that the chitolytic properties of the chitinase might tend to degrade samples stored for longer periods of time.

G. Wagner et al., "Chitin in the Epidermal Cuticle of a Vertebrate (*Paralipophrys trigloides*, Blenniidae, Teleostei)," Experentia, vol. 49, pp. 317–319 (1993) reported finding the presence of chitin in the epidermal cuticle of a bony fish.

There is a continuing need for new methods for diagnosing fungal infections in plant, animal, and human tissue samples and fluids.

Marine bacteria of the genus Vibrio produce many proteins related to chitin degradation and assimilation, including cell-surface, $Ca^{++}$-dependent lectins; endo- and exo-chitinases; endo-chitodextrinases; and exo-$\beta$-N-acetylglucosaminidases (N,N'-diacetylchitobiose hydrolases). Normally found in environments rich in chitin originating from plankton, arthropods, or fungi, Vibrio bacteria are chitinoclastic (chitinivorous), and have been reported to utilize N-acetylglucosamine as a carbon source as efficiently as *E. coli* metabolizes glucose.

It has been proposed that when a Vibrio approaches a chitin nutrient source, a cell-surface, calcium-dependent lectin temporarily attaches the Vibrio to the chitin. A secreted chitinase then breaks down chitin to produce chitodextrins $[(GlcNAc)_n]$, which diffuse into the periplasmic space. In the periplasmic space chitodextrinase degrades the oligomers to $(GlcNAc)_2$ dimers. Either an N,N'-diacetylchitobiose permease transports this disaccharide to the cytoplasm for hydrolysis by a separate cytoplasmic exo-$\beta$-N-acetylglucosaminidase (N,N'-diacetylchitobiase) followed by phosphorylation; or alternatively a periplasmic endo-chitodextrinase and a periplasmic exo-$\beta$-N-acetylglucosaminidase split N,N'-diacetylchitobiose to the monosaccharide N-acetylglucosamine, a sugar that can be used in the phosphotransferase system (PTS).

C. Yu et al., "The Sugar-Specific Adhesion/Deadhesion Apparatus of the Marine Bacterium Vibrio furnissii is a Sensorium that Continuously Monitors Nutrient Levels in the Environment," Biochem. Biophys. Res. Commun., vol. 149, pp. 86–92 (1987); and C. Yu et al., "Chitin Utilization by Marine Bacteria," J. Biol. Chem., vol. 266, pp. 24260–24267 (1991) disclose a calcium-dependent mannose-favoring cell surface lectin in *V. parahemolyticus*; and a calcium-dependent lectin in *V. furnissii* that binds to glycosides of GlcNAc (preferred ligand), as well as to glycosides of mannose and glucose.

Lectins have been alternatively defined (1) as carbohydrate-binding proteins or glycoproteins of non-immune origin that agglutinate cells or that precipitate glycoconjugates; or (2) simply as carbohydrate-binding proteins of non-immune origin. Lectins have been isolated from a wide variety of organisms, including bacteria, invertebrates, vertebrates, and plants. Lectins are often glycosylated, and are frequently composed of homo- or heterodimers with one binding site per subunit.

Very few non-catalytic, chitin-binding lectins have been isolated from bacteria. None has ever previously been isolated from Vibrio. D. Mirelman et al., Chapter 1 in D. Mirelman (ed.), Microbial Lectins and Agglutinins (1986) report that *Chlamydia trachomatis*, *Bordetella bronchiseptica*, *Pasteurella multocida*, and *Streptococcus salivarius* express substances that specifically bind to GlcNAc. The association of these activities with particular cellular structures has not been established. Some plant lectins are specific for GlcNAc, for example wheat germ agglutinin (WGA) and tomato lectin; most are non-specific in the sense that they bind compounds other than chitin, for example, sialic acid and polylactosamines. Many bind to smaller molecules as well as to polymers. Plant-derived, chitin-binding proteins are disclosed in M. Chrispeels et al., "Lectins, Lectin Genes, and Their Role in Plant Defense," Plant Cell, vol. 3, pp. 1–9 (1991); J. Huesing et al., "Effect of Wheat Germ Isolectins on Development of Cowpea Weevil," Phytochemistry, vol. 30, pp. 785–788 (1991); J. Van Parijs et al., "Hevein: An Antifungal Protein from Rubber-tree (*Hevea brasiliensis*) Latex," Planta, vol. 183, pp. 258–264 (1991); W. Broekaert et al., "A Chitin-Binding Lectin from Stinging Nettle Rhizomes with Antifungal Properties," Science, vol. 245, pp. 1100–1102 (1989); and J. Huesing et al., "Rice and Stinging Nettle Lectins: Insecticidal Activity Similar to Wheat Germ Agglutinin," Phytochemistry, vol. 30, pp. 3565–3568 (1991).

A novel, calcium-independent, soluble, Vibro-derived, chitin-binding protein has been discovered, and has been given the name "chitovibrin." The native function of chitovibrin is currently unknown, but the protein is not catalytic—in particular, chitovibrin does not degrade chitin. Following the addition of chitin, chitin oligomers, or cellobiose to the growth medium, chitovibrin is inducibly and copiously secreted by *Vibrio parahemolyticus*, in amounts that are similar to and are in concert with the secretion of endo-chitinase.

Chitovibrin may be used as the basis for a non-degrading, easy-to-use stain for diagnosing fungal infections, including yeast infections, in plant, animal, and human tissues or fluids. (Plant materials may include living tissues, as well as grains, fruits, vegetables, tubers, and other agricultural products.) The diagnostic method is simple, rapid, sensitive, and general. Chitovibrin specifically stains fungal cell walls or yeast bud scars with high sensitivity. A filter assay, enzyme-linked system will detect small amounts of fungal cell wall or yeast bud scar materials present in body fluids, other fluids, potable water samples, or beverages. An air filter assay, using enzyme-linked or chromogenic systems, will detect small amounts of fungal cell wall or yeast bud scar materials in air filters, which can also be contaminated with fungi and their spores. Likewise, fungal contamination in contact lenses or other prostheses can be assayed.

This assay, analogous to ELISA, can for example use an immobilized chitovibrin that is placed in contact with a sample. After rinsing unbound sample away, adherent chitin fragments will bind mobile, enzyme-linked chitovibrin, for example, a chitovibrin linked to horseradish peroxidase. The unbound enzyme-linked chitovibrin is washed away, and chitin is detected by reaction of the linked enzyme with a suitable substrate.

The avidity of chitovibrin for chitin is much higher than the avidity of anti-chitin antibodies, and chitovibrin exhibits chitin-binding activity over a wider range of salt concentrations (up to at least 4 M NaCl), pH's (at least from pH 4 to pH 11), and temperatures (up to at least 55° C.). Compared to antibody-based assays, less chitovibrin is needed per assay, and the detection sensitivity of chitovibrin is higher. In addition, because chitovibrin is copiously secreted by at least some strains of Vibrio bacteria under suitable culture conditions, production costs are considerably lower than those for anti-chitin antibodies.

A wide variety of fungal infections may be detected using chitovibrin as a stain. This test allows an early and definitive diagnosis of fungal organisms causing opportunistic infections, so that an appropriate antifungal therapy can be initiated promptly. For example, the assay recognizes yeasts by visualizing chitin that is present in yeast bud scars.

Polymeric chitin is produced neither by mammals nor by higher plants, although (as discussed by Wagner et al., cited above) chitin may be present in some fish, Any chitin found in a mammalian host is necessarily of non-mammalian origin, and (other than in the digestive tract) implies the presence of an infection. Natural chitin sources other than fungi include a number of invertebrates; chitin is notably found in the exoskeletons of arthropods. These potential non-fungal sources of chitin should not significantly interfere with the use of chitovibrin to identify fungal infections.

Chitovibrin, preferably conjugated to a label, can be used to detect the presence of intact fungal organisms or fragments of chitinous cell walls. Especially if conjugated to an enzyme to amplify the detection signal (analogous to ELISA), chitovibrin will detect fragments of chitinous cell walls or yeast bud scars in circulation, even in cases where the fragments alone could not be used to culture the infecting organism. For example, the presence of chitin in etiologic agents of mycoses from tissue specimens may be verified by a system such as chitovibrin/rabbit anti-chitovibrin antibody/fluorescent-labeled goat anti-rabbit antibody; or a system such as chitovibrin directly coupled to fluorescein isothiocyanate (FITC); or an enzyme-linked system such as horseradish peroxidase, alkaline phosphatase, or β-galactosidase directly coupled to chitovibrin, or an indirect antibody assay.

Chitin is present in the cell walls of most pathogenic fungi during at least one stage of the fungal life cycle, or in yeast is present in bud scars. A chitin-specific chitovibrin stain will therefore be specific for fungi (chitin being generally absent from bacteria and infectious protozoans), and will be a broad spectrum stain for most kinds of fungi. Fortunately, many current treatments for systemic fungal infections, for example amphotericin-B and azoles, are broad-spectrum in effect. A rapid, sensitive, and accurate diagnostic method that provides an early, definitive diagnosis of disease-causing fungal organisms (perhaps without the need of a species-specific classification) will be more beneficial for patients (particularly AIDS patients and bone marrow transplant patients), than other less sensitive or more time-consuming processes that attempt to identify particular species. Morphology of the fungal organisms delineated by a chitovibrin label generally provides sufficient information to identify the genus of the organisms. Species-specific identification, if needed, can be made at a later opportune time using other conventional methods, such as blood cultures. The course and efficacy of an antifungal treatment can readily be monitored with the chitovibrin-staining technique.

It may be difficult in some cases to distinguish between normal surface flora and disseminated deep infections in histological samples, smears, and other superficial samples from oral-esophageal fungal infections. A large number of samples from this kind of infection, such as candidosis, will be inspected to establish differences between samples from the Candida, and those of normal mucosal flora.

A chitovibrin filtration assay of body fluids may reduce the need for the invasive biopsy procedures that were previously required for a proper diagnosis in many immunodepressed hosts.

Organisms

Wild-type *V. parahemolyticus* isolates, for example ATCC strain 27969 and other *V. parahemolyticus* strains, were grown on 804 medium (i.e., distilled water with 0.75 g/l KCl, 6.9 g/l $MgSO_4$, 23.4 g/l NaCl, 1 g/l tryptone, and 1 g/l yeast extract), and 0.5% (w/v) swollen practical-grade chitin. Cells were harvested after the visible chitin particles had been hydrolyzed. Isolates were preserved at −70° C. in 804 medium (without chitin) with 30% glycerol.

Chemicals and reagents

Protein assay reagents, ion-exchange resins, and gel filtration resins were obtained from Bio-Rad (Richmond, Calif.). Chitin, chitosan, buffers, electrophoresis standards, dipalmitoylphosphatidylethanolamine, and p-nitrophenyl butyrate were obtained from Sigma (St. Louis, Mo.). Acrylamide:bis-acrylamide solution (37.5:1) was obtained from Amresco (Solon, Ohio). Tritiated acetic anhydride and $Na^{125}I$ were obtained from ICN Biomedicals (Costa Mesa, Calif.). Iodo-beads used in protein radioiodination were obtained from Pierce (Rockford, Ill.). Thin-layer chromatography silica gel G plates were obtained from Analtech (Newark, Del.). Sepharose 4B, 6B and Sephadex G-75 were obtained from Pharmacia Fine Chemicals (Uppsala, Sweden).

Pretreatment of chitin

Swollen chitin was prepared from crab chitin (Sigma, practical grade) by treatment with phosphoric acid, following the procedures of J. Monreal et al., *Can. J. Microbiol.* vol. 15, 689–696 (1968).

Tritium-labeled chitin

Tritiated chitin was prepared by N-acetylation of chitosan with [$^3$H]-acetic anhydride, following the procedures of E. Cabib, *Meth. Enzymol.*, vol. 161, pp. 424–426 (1988). Before acetylation, commercial chitosan usually required further deacetylation to make it more reactive; this deacetylation followed the procedures of S. Mima et al., *J. Appl. Poly. Sci.*, vol. 28, pp. 1909–1917 (1983). The specific activity of the tritiated chitin was 0.5 μCi/mg chitin, corresponding to approximately 0.1 μCi/μmole GlcNAc.

Chitin oligomers

Chito-tetramer, -pentamer, and -hexamer were purchased from Seikagaku (Ft. Lauderdale, Fla.). Larger chitin oligomers were prepared by hydrolysis of purified, commercial chitin, either with HF or HCl, according to the procedures of C. Bosso et al., *Carbohydr. Res.*, vol. 156, pp. 57–68 (1986); or J. Rupley, *Biochim. Biophys. Acta*, vol. 83, pp. 245–255 (1964). The latter method resulted in partial de-N-acetylation of the resulting oligomers. Contaminating amino acids and salts were removed during the first two steps of elution from activated charcoal, which was used to trap oligomers following dilution of the hydrolysate. Chitin oligomer preparations were fractionated on a Bio-Rad Bio-Gel P-6DG desalting gel column (3.5×83 cm), and were eluted with 50 mM ammonium acetate to minimize clustering of oligomers under low ionic strength conditions. A finer purification of the oligomers was accomplished by repeated chromatography on a Bio-Rad Bio-Gel P-4 gel column (1×113 cm).

Immobilization of chitin oligomers.

After the Bio-Gel P-6DG desalting gel column purification step, chitin hydrolysate fractions containing mixtures of higher oligomers were pooled and bound to aminobutylamino-agarose by reductive amination. Twenty mg of high molecular weight chito-oligomers (MW ranging from 1,000 to 3,000) were resuspended in 0.2 M borate buffer, pH 9.5, and were incubated for 42 hours at 50° C. with 6 ml of aminobutylamino-agarose gel and 25 mg sodium cyanoborohydride. After acidification with 0.5 M HCl and drying under a vented hood, boric acid was removed by co-evaporation with methanol, and the gel was washed extensively with 10 mM phosphate buffer, pH 6.

Chitinase activity

Chitinase activity was measured as described by the procedures of J. Molano et al., *Anal. Biochem.*, vol. 83, pp. 648–656 (1977); and E. Cabib, *Meth. Enzymol.*, vol. 161, pp. 424–426 (1988); with minor modifications. Tritiated chitin (190 $\mu$L, adjusted to 90,000 cpm/$\mu$mole GlcNAc) was incubated at 45° C. with 10 $\mu$l of enzyme preparation for 10 minutes. The reaction was stopped by the addition of 200 $\mu$l 20% trichloroacetic acid. The mixture was then centrifuged for 2 minutes, and 100 $\mu$l of the clear supernatant fraction was radioassayed.

Antibodies

Contaminating 95 kDa *V. parahemolyticus* chitinase was removed from purified chitovibrin concentrates by Sepharose-chitinase antibody affinity chromatography. Anti-chitinase polyclonal antisera were obtained from rabbits inoculated with a cloned chitinase to avoid the production of any chitovibrin-specific antibodies. Antisera were purified by the procedures of N. Chua et al., Chapter 85, pp. 1063–1080 in Edelman et al. (eds.), *Methods in Chloroplast Molecular Biology* (1982); and P. Maurer et al., *Meth. Enzymol.*, vol. 70, pp. 49–70 (1980). The cloned chitinase was obtained as described in U.S. Pat. No. 5,352,607. Anti-chitinase antibody purification was performed with immobilized cloned chitinase: 5 mg of cloned chitinase, dissolved in 20 ml of 0.1 M sodium bicarbonate, was attached to 25 ml of wet Sepharose 4B by cyanogen bromide activation, packed in a column (1.5 ×3.5 cm), washed, and used to affinity-purify anti-chitinase IgG.

Immobilization of anti-chitinase antibodies

A 22 ml preparation of affinity-purified anti-chitinase antibodies (0.439 mg/ml) was immobilized on 50 ml of wet Sepharose 4B activated with 1.4 mg of cyanogen bromide, following the procedures of P. Dean et al., pp. 31–59 in P. Dean et al. (eds.), *Affinity Chromatography—a Practical Approach* (1985). Then 100 ml of 1 M glycine were added to block the remaining active sites on the gel, after which the gel was washed with 10 mM phosphate buffer, pH 6. Measurements of the protein content of the original preparation and of the solution after binding showed nearly quantitative immobilization of the antibodies on Sepharose.

Preparation of neoglycolipids

The procedures of M. Stoll et al., *Biochem. J.*, vol. 256, pp. 661–664 (1988) were followed, with modifications due to the low solubility of higher chitin oligomers in non-aqueous solvents. Five $\mu$moles of lyophilized N-acetyl glucosamine oligomer were dissolved at 65° C. in 0.5 ml of 5% lithium chloride in N,N'-dimethylacetamide for 12 hours, as in the procedures of C. McCormick et al., *J. Poly. Sci. Poly. Lett. Ed.*, vol. 17, pp. 479–484 (1979). The oligomer solution was mixed with 5.24 ml of a 5 mg/ml solution of dipalmitoylphosphatidylethanolamine in chloroform:methanol (1:1), sonicated for 10 minutes, and incubated for 2 hours at 65° C. After adding sodium cyanoborohydride (1.2 mg) in methanol (120 $\mu$l), the mixture was incubated at 65° C. for an additional 16 hours. Excess cyanoborohydride was destroyed with 0.5 M HCl, the sample was neutralized with ammonium bicarbonate, and boric acid was co-evaporated with methanol under nitrogen. The dried product was redissolved in chloroform:methanol:$H_2O$ (15:70:30) and applied to a disposable silica-$C_{18}$ column that had been washed with the same solvent. The product was eluted with chloroform:methanol:$H_2O$ (60:35:8), following the procedures of A. Lawson et al., *Carbohydr. Res.*, vol. 200, pp. 47–57 (1990). Binding activity was tested with radiolabelled wheat germ agglutinin (WGA) in a 96-well plate. Yield of neoglycolipids was determined with p-dimethyl-amino-benzaldehyde (DMAB), following the procedures of J. Reissig et al., *J. Biol. Chem.*, vol. 217, pp. 959–961 (1955), with modifications for hexosamines: 100 $\mu$l aliquots of the samples were dried at room temperature, and were incubated at 37° C. for 4 hours with 100 $\mu$l of a 0.01 unit/ml chitobiase solution. (1 unit corresponds to the hydrolysis of 1 $\mu$mole PNP-$\beta$-GlcNAc per minute.) After adding 20 $\mu$l of 0.8 M potassium tetraborate, pH 9.5, the samples were boiled for 3 minutes, cooled, and 750 $\mu$l of DMAB reagent was added. After incubation at 37° C. for 30 minutes, absorbance at 585 nm was measured.

96-well plate binding assay

Neoglycolipid solutions were air-dried in triplicate in 96-well plates. Then 300 $\mu$L/well of a 1.5% bovine serum albumin blocking solution (for non-specific protein-binding) was added, and the plates were incubated for 2 hours at 25° C. on a shaker. The wells were then washed with distilled water, and incubated for 2 hours at 25° C. with 60,000 to 100,000 cpm of $^{125}$I-chitovibrin in 300 $\mu$l 1.5% bovine serum albumin ("BSA"), After removing the labeled solution, the wells were washed for 20 minutes with 250 $\mu$L phosphate-buffered saline ("PBS"), and rinsed with distilled water. Then 200 $\mu$l 6 M guanidine-HCl was added to each well, the wells were incubated for 10 minutes at 25° C., and the wells were removed and radioassayed.

pH-dependent binding assays

One hundred $\mu$l of an aqueous 2 g/l suspension of regenerated chitin was centrifuged for 2 minutes in a minicentrifuge, the supernatant fraction was removed, 50 $\mu$l of buffer of the desired pH was added, and the suspension was mixed by vortexing. Radiolabelled chitovibrin was added, and the sample was vortexed and incubated at 4° C. for 30 minutes. After centrifuging, the pellet was rinsed with water and boiled with loading buffer+2-mercaptoethanol, and then electrophoresed. The gel was stained, destained and dried. After autoradiography, relative binding was assessed by densitometry.

Western-blot analysis

Transfer of proteins onto polyvinylidene fluoride membranes followed the procedures of P. Matsudaira, *Meth. Enzmol.*, vol. 182, pp. 602–613 (1990). Proteins were electrophoresed on a 6% sodium dodecyl sulfate-polyacrylamide gel (SDS-PAGE) after a 20 minute pre-run on the gel with a sodium thioglycolate solution. Proteins were transferred onto the membrane at 40 V and 0.68 Ampere-hour. Membranes were then incubated with diluted (1:100) antiserum for 90 minutes, treated with radiolabelled protein A according to the procedures of W. Burnette, *Anal. Biochem.*, vol. 112, pp. 195–203 (1981), and were allowed to expose X-ray film at −70° C. for 3–18 hours

Chitin affinity chromatography

To test for chitin binding, protein preparations were passed through regenerated chitin, prepared as described above.

Gel permeation chromatography

Size-exclusion columns were eluted with 10 mM potassium phosphate buffer, pH 6. A rough separation of chitin oligosaccharides was performed on P-6DG desalting-gel (4.5×42 cm). Further purification was accomplished on Bio-Gel P-4 (0.8 ×85 or 113 cm).

Hydrophobic interaction chromatography 3 ml of Phenyl-Sepharose-CL 4B was packed into a column (0.8×6 cm). Sodium chloride concentration was brought to 4 M before samples were loaded onto the column, which was equilibrated with 4 M salt buffer. Samples were eluted with gradients of decreasing salt concentration, following the procedures of R. Kennedy, *Meth. Enzymol.*, vol. 182, pp. 339–343 (1990).

Radiolabelling of protein with $^{125}$L

A 100 μl aliquot of 0.18 mg/ml chitovibrin solution was incubated for 5 minutes at 25° C. with 1 mCi of $Na^{125}I$ and 2 Iodo-beads (Pierce Chemical Co.) in 100 μl Tris-HCl buffer, pH 7.5. (Iodo-beads comprise chloramine-T oxidizer bound to glass beads.) A Pharmacia PD-10 column, Sephadex G-25 M, bed height 5 cm, was used to collect 0.6 ml fractions of eluent. Three samples were analyzed for $^{125}I$. Specific activity was measured as $3.2 \times 10^6$ cpm/μg protein.

Isoelectric focusing

Isoelectric focusing gels were prepared with 2.8 g sucrose, 3.1 ml 40% acrylamide/bis-acrylamide solution (37.5:1), 2 ml of ampholines (pH 3–7), 80 μl ammonium persulfate, and distilled $H_2O$ to 25 ml. After electrophoresis, the gel was washed to remove ampholines, and stained following the procedures of U. Laemmli, *Nature*, vol. 227, pp. 680–685 (1970).

General methods

Protein content was determined by the procedures of M. Bradford, *Anal. Biochem.*, vol. 72, pp. 248–254 (1976), using 1 ml of a 5× diluted Bio-Rad protein assay reagent and 100 μl of sample. The SDS-PAGE experiments (usually 7.5% or 6%) were performed according to the procedures of U. Laemmli, *Nature*, vol. 227, pp. 680–685 (1970). Gels were stained for 30–60 minutes with 0.1% Coomassie Blue R in 50% methanol/$H_2O$. Destaining was accomplished with several changes of methanol/acetic acid/$H_2O$ (2:1:7).

Induction of chitinase and chitovibrin expression

Cultures of *V. parahemolyticus* (35 ml) were grown in 125 ml Erlenmeyer flasks with 804 medium or M9CA (minimal) medium supplemented with particular oligosaccharides (as discussed below) at 1.25 mg/ml. After 15 hours, supernatant fractions were precipitated with 50% ammonium sulfate, dialyzed, and analyzed for chitinase by electrophoresis on a 6% SDS-PAGE gel.

When *V. parahemolyticus* was grown in 804 medium supplemented with chitin, 95 kDa and 134 kDa polypeptides appeared in the medium about 36 hours after inoculation (molecular weights as determined by sodium dodecyl sulfate-polyacrylamide gel electrophoresis). The contemporaneous appearances of the 95 kDa and 134 kDa proteins were concomitant with the appearance of chitinase activity. The 95 kDa band was therefore attributed to chitinase, and the 134 kDa band was attributed to the novel protein that has been named "chitovibrin." These proteins could be purified by chitin affinity chromatography. The presence of calcium was not necessary for either of the proteins to bind chitin.

Induction of the two proteins by various saccharides was tested on 15-hour *V. parahemolyticus* cultures grown on media supplemented with 1.25 mg/ml of various saccharides. Expression of both chitinase and chitovibrin were induced by the addition of chitin, chitobiose, N-acetylglucosamine, or cellobiose to the medium. Among a large number of oligosaccharides tested other than the chitin oligomers, only cellobiose was observed to induce expression of chitinase and chitovibrin, although neither protein showed any affinity for cellulose.

Gel filtration

Chitovibrin stained with Coomassie Blue as a 134 kDa protein band on SDS polyacrylamide gel. The 95 kDa chitinase and the 134 kDa chitovibrin were difficult to resolve by gel permeation. Separation of the proteins could be partially accomplished on Bio-Gel P-200 (1.5 ×110 cm) eluted with 50 mM potassium phosphate buffer, pH 6, collecting 2.8 ml fractions. Both proteins eluted from the column with apparent molecular weights larger than those suggested by the values obtained from gel electrophoresis, but not high enough to suggest the formation of multimers at low salt concentrations. Elution of the proteins with 0.3% octyl β-glucoside gave somewhat better separation, indicating a possible hydrophobic interaction between the proteins.

Immunoaffinity chromatography

To remove traces of chitinase activity from chitovibrin, gel-filtration-purified samples were run through a column of immobilized, affinity-purified anti-chitinase antibodies. Polyclonal rabbit antibodies against the cloned chitinase were specific for chitinase and did not bind chitovibrin, as was shown by blots on gels containing both chitinase and chitovibrin. Most of the chitinase in the original preparation was removed by the Sepharose-anti-chitinase affinity column. Proteins bound to the affinity gel were released with 6 M guanidine-hydrochloride. A 65 kDa, proteolytic N-terminal chitinase fragment with poor binding to polyclonal anti-chitinase was also observed. Ouchterlony double-diffusion gels confirmed that chitinase and chitovibrin are antigenically different. At this point of purification, the chitovibrin was electrophoretically homogeneous, and the apparent molecular weight was 134 kDa. Overall yields for purified chitovibrin were below 10% due to the difficulty of separation from chitinase.

Chitovibrin can be separated from the 95 kDa chitinase that is simultaneously secreted by *V. parahemolyticus* by other techniques as well, such as differential elution from chitin matrix columns, gel permeation, or electrophoresis. However, neither ion-exchange chromatography nor phenyl-Sepharose chromatography were found to be useful in separating chitinase from chitovibrin.

Affinity to chitin and chitin-oligomers

A 1 ml column of regenerated chitin was used for affinity chromatography of a chitovibrin-enriched sample that had been radiolabelled with $^{125}I$. Autoradiograms showed that chitovibrin bound to the chitin, but that it could be eluted with concentrated chitin oligosaccharides at approximately 30 mg/ml (about 20–30 mM). Calcium was not required for the chitovibrin to bind chitin in any of the assays.

The binding of chitovibrin to chitin was further analyzed by elution with a step gradient of guanidine-HCl. A 10 ml sample of chitinase/chitovibrin was loaded on a 3 ml column of regenerated chitin. The column was washed with 8 ml of PBS, and was then eluted with 1 ml batches of guanidine-hydrochloride in concentrations ranging from 0.12 M to 6 M. Eluted fractions were dialyzed against distilled water. Analysis of the eluted fractions on 6% SDS-PAGE indicated that chitinase was released at lower concentrations of guanidine-hydrochloride than chitovibrin. An 80–85 kDa protein, not seen either in the original sample, or in affinity experiments with pure chitinase, co-eluted with chitovibrin. Although this hypothesis has not yet been confirmed, the 80–85 kDa protein is believed to be an endogenous-protease-induced, proteolytic breakdown product of chitovibrin, having equally strong chitin binding properties as chitovibrin. In addition, it is expected that other, smaller peptide fragments of chitovibrin will exhibit similar chitin-binding properties, and could be used in coupling to detection systems.

Bound chitovibrin could not be released from chitin with 4M NaCl, or by changing the pH from about 4 to about 11.

A sepharose/chito-oligomer affinity gel (1 ml) was prepared with mixed chitin oligomers, dp5–20 (where "dp" denotes the degree of polymerization of the oligomer.) $^{125}$I-labeled chitovibrin was loaded onto the column, which was then washed with a low-salt buffer, followed by step-wise elution with 2N NaCl and 6 M guanidine-hydrochloride. Autoradiography analysis of eluted fractions indicated a strong, salt-resistant binding of chitovibrin to the chitodextrins. Although the chitodextrin-binding capacity of chitovibrin was lost by denaturation in 6 M guanidine-hydrochloride, the binding ability was regained after dialysis against distilled water.

Binding to chitodextrin neoglycolipids

The binding affinity of chitovibrin to chitodextrins as a function of the degree of polymerization of the chitodextrin was examined using synthetic chitin oligomer neoglycolipids (sugars synthetically bound to phosphatidyl ethanolamine). Binding of radiolabelled chitovibrin was examined at pH 8.8 on 96-well plates. Wells were coated with chitodextrin neoglycolipids ranging from dp3 to dp12, with triplicates of each neoglycolipid. A chitovibrin sample from fraction 60 off the Sephadex column (2.8 ml per fraction) was radiolabelled in the presence of chitin oligomers (to protect the binding site), and 50 µl of the labeled protein (100 cpm) was placed in each well. A neoglycolipid prepared from lactose was used as a negative control—no binding was observed for this negative control. Chitovibrin appeared to bind most avidly to chitodextrin neoglycolipids with dp >10, or with intact oligomers of dp >9. (The reducing terminal was linearized by the reductive amination.) Significant binding occurred with dp8 and dp9 neoglycolipids, and dp4 gave increased binding above background. While the weak dp4 binding is not understood, it is speculated that 2–3 dp4 units from the multimeric neoglycolipid surface may fit into the chitovibrin binding site. Radiolabelling chitovibrin with $^{125}$I appeared to reduce its binding capacity, consistent with the hypothesis that tyrosine is important in the binding site.

Cellulose oligomers were not tested because chitovibrin showed no binding to cellulose. β-mannans were not tested.

pH optimum and pI

Binding of chitovibrin to chitin was examined over a pH range from 3.6 to 10.8 with radiolabelled, purified chitovibrin. Binding occurred over at least the range from about pH 4 to about pH 11, with a maximum near pH 6.0. Chitovibrin has an isoelectric pH (pI) near 3.6.

N-terminal sequence

After transfer onto polyvinylidene fluoride membranes, the first twenty-five amino acids of the N-terminal sequence of chitovibrin were determined with an automated protein sequencer to be AVDAAPLEVYDSNKVYNGGDQVQHE (SEQ ID NO. 1). These N-terminal 25 amino acids were compared with published sequences in the Genbank database. The 25 A.A. segment showed up to 73% homology with internal sequences from tubulin from several organisms; and higher homologies with internal sequences from: (1) a sucrose-6-phosphate hydrolase from V. alginolyticus (Poisson probability P=0.99); (2) a pilus biogenesis protein from V. cholera (P=0.99); and (3) a chitinase from an Alteromonas species (P=0.74); and lower homologies with various other proteins. No homology was apparent with the already-determined complete sequence of the V. parahemolyticus soluble endo-chitinase (see U.S. Pat. No. 5,352,607). In addition, tryptic peptide-HPLC maps of the two proteins showed no similarity (data not shown).

Because of its inducibility by chitin fragments, chitovibrin is probably not responsible for the initial binding of the bacterium to chitin, unless it is expressed in a different form attached to the cell surface. The N-terminal sequence of the secreted protein begins with alanine, suggesting that a signal sequence cleavage has occurred, consistent with a secreted protein, and arguing against simple release from dying cells. By contrast, the V. parahemolyticus and other Vibrio cell surface lectins reviewed and examined by C. Yu et al., "Chitin Utilization by Marine Bacteria,"J. Biol. Chem., vol. 266, pp. 24260–24267 (1991) were all as-yet-uncharacterized, calcium-dependent, cell-surface, small-carbohydrate-binding molecules that may be responsible for the initial binding of chitin substrates.

Molecular Cloning

Using techniques that are now well-known in the art (see, e.g., J. Sambrook et al. (eds.), Molecular Cloning: A Laboratory Manual (2nd ed. 1989)), this 25-amino acid partial sequence will be used to design polymerase chain reaction primers to amplify the gene encoding the chitovibrin protein; and the isolated gene will be cloned and over-expressed in E. coli for large-scale production of chitovibrin. Even prior to the completion of this cloning, chitovibrin may be prepared and isolated by direct induction of expression in V. parahemolyticus, as described above.

Fungal Diagnosis

Isolated chitovibrin was coupled through standard techniques to fluorescein isothiocyanate (FITC) in phosphate buffer (pH 9), and the labeled chitovibrin was purified (i.e., separated from the labeling reagents and any uncoupled chitovibrin) by gel permeation chromatography. The labeled chitovibrin was then used to stain an air-dried smear sample of an uncharacterized filamentous fungus that had been grown on nutrient agar. The dried fungus was mounted on a glass slide. Any accessible fungal proteins on the slide were blocked with a 1% solution of BSA, and the slide was washed with PBS (pH 7). Fifty µL of the chitovibrin-FITC conjugate was placed in contact with the specimen for thirty minutes, after which the slide was washed with PBS. PBS-glycerol was added to the slide, and the slide was photographed using standard fluorescence microscopy techniques, and filters specific for the fluorescence wavelength of fluorescein. Filamentous fungi were easily and clearly visualized in the resulting micrographs.

The chitovibrin fungal diagnostic system will be confirmed in plant, animal, and human tissue sections with known fungal infections that have previously identified by GMS or other tests. For example, tissue sections from animals with aspergillosis, cryptococcosis, and blastomycosis; tissue samples from human AIDS patients with candidosis-I; and tissue samples from maize or peanut plants, and their respective grains, infested with *Aspergillus flavis* will be tested with a chitovibrin/anti-chitovibrin antibody probe, or with a chitovibrin direct conjugate probe, and examined under a light microscope or a fluorescent microscope.

The spectrum breadth of the chitovibrin diagnostic probe will be confirmed by identifying chitin in the fungal cell walls or yeast bud scars of the most common opportunistic fungi and true pathogenic fungi in samples from human patients, and in samples from plants and animals of economic significance. The present invention can be used to verify the presence of chitin in these organisms in samples prepared in thin sections. Chitinous fungi will be categorized separately from non-chitinous fungi, if any of the latter are found in this screening. It is expected that the accessibility of chitin may in some cases be partially or totally blocked by the polysaccharide capsule found in some fungi, such as that of Cryptococcus. Establishing the extent of this blockage will help to improve the diagnostic system. For example, proteases or polysaccharidases such as a glucanase or mannanase may be used as an adjuvant to uncover chitin in a complex cell wall, to facilitate accessibility to chitovibrin. Alternatively, a 1–5% periodate solution can be used to digest the polysaccharide capsule. Furthermore, even in a single infection, the biochemical components of Cryptococci can vary over the course of the life cycle. Thus at least some Cryptococci should be accessible to this diagnostic method at any given time, even if the polysaccharide capsule blocks the accessibility of chitin in some of the organisms.

Opportunistic fungal organisms are generally nonpathogenic in hosts with healthy immune systems. The validity of this diagnostic system will be confirmed with a variety of opportunistic fungal organisms, including those most commonly found in AIDS patients. Tissue preparation prior to staining will be conducted in accordance with standard procedures for fixed, paraffin-embedded tissues. The cells will be fixed with either methanol or 4% paraformaldehyde. The specimen will be embedded in paraffin and thin-sectioned. After a series of standard deparaffination procedures with xylene and a series of ethanol solutions at different concentrations, chitovibrin (100 $\mu$l of 1.0 mg/ml solution) and diluted, labelled anti-chitovibrin (100 $\mu$l of a 1 to 10 $\mu$g/ml solution) will be applied to BSA-pretreated specimens. Each specimen will be washed with PBS between additions of reagents. Endogenous peroxidase in the specimen will be removed if peroxidase conjugate is used as the labeling probe. Several labeling probes will be investigated, to identify an optimal label for these tests. For example, the efficacy of Protein A-Peroxidase or Protein A-FITC conjugate, anti-rabbit IgG-Peroxidase or FITC conjugate, peroxidase-antiperoxidase complex, and avidin-biotin will be evaluated. It may be advantageous to label the chitovibrin directly with various labels known in the art, to eliminate the need for an anti-chitovibrin antibody. For example, direct conjugates of chitovibrin with FITC or with horseradish peroxidase will be examined. Whether the chitin-specific binding protein or its antibody is labelled, detectable labels that may be used are labels those known in the art, including a radioactive material, a fluorophore, a dye, an electron-dense compound, or an enzyme. The variety of potential label possibilities broadens the potential applications of this invention. A conventional GMS fungal stain will be used in parallel for comparison.

The diagnostic system will also be validated by testing chitinous materials in suspension, to demonstrate that the system also works in diagnosis with fluid samples of biological origin. A small filter unit (Spin-X, CoStar Co.) equipped with a polyvinylidene difluoride (PVDF, Immobilon, Millipore, USA) membrane pretreated with BSA will be used to retain chitinous materials, specifically swollen chitin in suspension. Other reagents in the diagnostic probe will be applied in the following order: chitovibrin, anti-chitovibrin antibody, and Protein A-Peroxidase conjugate. (The use of enzyme in place of FITC will allow quantitative analysis if desired.) After addition of a chromogenic developing solution (e.g., 4-chloro-N-naphthol and $H_2O_2$, or dyes such as CY5 (Amersham, Inc.)), only units with chitin, chitovibrin, and anti-chitovibrin should be positive. It should be feasible to retain chitinous fungal organisms, or their chitinous cell wall or yeast bud scar materials, on the membrane without interference by other proteins present in body fluids. Subsequently, the retained chitinous materials can be qualitatively detected by the diagnostic probe if desired: chitovibrin (with or without anti-chitovibrin antibody), and a chromogenic label conjugate.

The following method will be used to demonstrate further the feasibility of this technique for diagnosis in body fluids. A set of fungal organisms will be grown in suspension. The cells will be mixed with normal human serum, and processed using a small filter unit as the retention matrix. The smallest number of fungal organisms or the smallest amount of fungal cell wall or yeast bud scar materials in 100 $\mu$l of serum giving a definitive result will be determined. The contaminated serum will be diluted for easy filtration, and prospective fungal organisms or fragments of cell walls or bud scars trapped by the membrane will be fixed with either methanol or paraformaldehyde. The filter will be washed twice with distilled water to lyse red blood cells when dealing with actual specimens, and then washed three times with PBS plus 0.05% Tween 20, followed by the addition of 100 $\mu$l of chitovibrin (1.0 mg/ml) for 20 min at room temperature. (Digestion at a higher temperature will also be attempted.) After washing the filter with PBS, diluted anti-chitovibrin antibody (100 $\mu$l) will be added to the filter and incubated for 30 min at room temperature. A labeled probe will be added to the filter after washing. Quantitative analysis can be achieved by using an appropriate labeled probe. If peroxidase is used in conjugation, a soluble chromogenic developing solution with ABTS can be used for quantitative analysis. Direct conjugates of chitovibrin will also be used in this study. To test that the system is specific for fungal organisms, several control groups will be tested as well. These control groups will include serum contaminated with other known bacteria, viruses, or protozoa. Alternatively, direct labelling of chitovibrin with visible dyes will be used for light microscopy and flow detection systems.

For example, fragments of Aspergillus cell wall, mycelial fragments obtained by sonication, and whole cells will each be suspended separately, and the suspensions diluted ten or more times. Each resulting solution will be filtered through a 10,000 molecular weight cut-off filter. Chitovibrin, rabbit anti-chitovibrin antibody, and horseradish peroxidase-labelled goat anti-rabbit IgG will be applied to the filters (a direct conjugate will also be used), and the catalytic potential of the bound enzyme will be assayed to determine the sensitivity of the assay for cell wall fragments in body fluids.

It has previously been the case that certain deep invasive fungal infections could only be properly diagnosed by histologic examination. It is possible that certain fungal antigens or whole cells might substantially disappear from circulation during certain stages of disease. In such cases it would still be desirable and safer to obtain a definitive diagnosis by testing body fluids if possible, rather than by examining histologic specimens. Comparisons will therefore be made between the effectiveness of chitovibrin as a diagnostic probe in samples of body fluids, with results from other diagnostic methods presently in use (including histologic identification if necessary).

Specimens collected from plants and animals will be processed appropriately for histologic identification by embedding and thin sectioning before specific staining procedures, with tissue samples prepared by standard protocols. Also, fluid samples will be processed for in vitro testing in a small filter unit using chitovibrin as a diagnostic probe. The procedures will be generally as described above. Correlation with other diagnostic procedures will be evaluated in a blind study with several control groups. Specimens from plants and animals with non-fungal infections, bacteremia, viral infection, and other disorders uncomplicated by fungal infections will also be tested as controls. Later, similar tests will be conducted with specimens from human patients, including AIDS patients and bone marrow transplant patients.

Although not tested as of the date this application is being filed, it is expected that homologous chitovibrin molecules may be isolated through similar methods from other Vibrio species.

As used in the claims below, a "substantially pure" chitovibrin (or a "substantially pure" peptide) is one in which any contaminants that may be present either: (1) are sufficiently low in concentration that there is negligible hydrolytic activity towards chitin, towards chitin oligomers, and towards chitobiose; or (2) are sufficiently low in concentration that only a single protein band is visible on SDS-PAGE.

The complete disclosures of all references cited in this specification are hereby incorporated by reference, as is the complete disclosure of the following paper—which is not prior art to this application: O. Gildemeister et al., "Chitovibrin: a chitin-binding lectin from *Vibrio parahemolyticus,*" *Glycoconjugate Journal*, vol. 11, pp. 518–526 (December 1994).

I claim:

1. A method for detecting chitin in a sample, comprising the steps of:

(a) contacting the sample with a substance comprising chitovibrin; and (b) inspecting the sample for the presence of chitovibrin bound to chitin, wherein bound chitovibrin indicates the presence of chitin in the sample;

wherein said chitovibrin is a protein of molecular weight about 134 kDa as determined by sodium dodecyl sulfate-polyacrylamide gel electrophoresis; wherein said chitovibrin has affinity for chitin and for chito-oligomers dp9 and larger; wherein said chitovibrin is obtained from or is identical to a protein obtained from secretions from marine bacteria of the genus Vibrio induced by the presence of chitin, chitin oligomers, or cellobiose; wherein said chitovibrin has an isoelectric pH of about 3.6; wherein said chitovibrin binds chitin at an optimum pH of about 6; wherein said chitovibrin binds to chitin in aqueous solutions throughout a range of NaCl concentrations from 0 M NaCl to about 4 M NaCl; and wherein said chitovibrin has no hydrolytic activity towards chitin, towards chitin oligomers, or towards chitobiose.

2. A method as recited in claim 1, wherein said chitovibrin is conjugated to a detectable label.

3. A method as recited in claim 2, wherein the detectable label is selected from the group consisting of a radioactive material, a fluorophore, a dye, an electron-dense compound, and an enzyme.

4. A method as recited in claim 1, wherein the sample comprises a plant tissue, an agricultural product, an animal tissue, a human tissue, a contact lens, a prosthetic device, or an air filter.

5. A method as recited in claim 4, wherein said inspecting step comprises inspecting the sample for the presence of chitovibrin bound to chitin in fungal cell walls.

6. A method as recited in claim 4, wherein said inspecting step comprises inspecting the sample for the presence of chitovibrin bound to chitin in yeast bud scars.

7. A method as recited in claim 1, wherein the sample comprises an animal body fluid, a human body fluid, a plant fluid, potable water, or a beverage.

8. A method as recited in claim 7, wherein said inspecting step comprises inspecting the sample for the presence of chitovibrin bound to chitin in fungal cell walls.

9. A method as recited in claim 7, wherein said inspecting step comprises inspecting the sample for the presence of chitovibrin bound to chitin in yeast bud scars.

10. A method as recited in claim 1, wherein said contacting step additionally comprises contacting the sample with a reagent comprising an antibody to chitovibrin.

11. A method as recited in claim 10, wherein said reagent additionally comprises a detectable label.

12. A method as recited in claim 11, wherein the detectable label is selected from the group consisting of a radioactive material, a fluorophore, a dye, an electron-dense compound, and an enzyme.

13. A method as recited in claim 10, wherein the sample comprises a plant tissue, an agricultural product, an animal tissue, a human tissue, a contact lens, a prosthetic device, or an air filter.

14. A method as recited in claim 13, wherein said inspecting step comprises inspecting the sample for the presence of chitovibrin bound to chitin in fungal cell walls.

15. A method as recited in claim 13, wherein said inspecting step comprises inspecting the sample for the presence of chitovibrin bound to chitin in yeast bud scars.

16. A method as recited in claim 10, wherein the sample comprises an animal body fluid, a human body fluid, a plant fluid, potable water, or a beverage.

17. A method as recited in claim 16, wherein said inspecting step comprises inspecting the sample for the presence of chitovibrin bound to chitin in fungal cell walls.

18. A method as recited in claim 16, wherein said inspecting step comprises inspecting the sample for the presence of chitovibrin bound to chitin in yeast bud scars.

19. A method for detecting chitin in a sample, comprising the steps of contacting the sample with a substance comprising a polypeptide, and inspecting the sample for the presence of said polypeptide bound to chitin, wherein bound polypeptide indicates the presence of chitin in the sample; wherein:

(a) said polypeptide has affinity for chitin and for chitooligomers dp9 and larger; and said polypeptide has no hydrolytic activity towards chitin, towards chitin oligomers, or towards chitobiose; and (b) said polypeptide is obtained from or is identical to a polypeptide obtained from the proteolytic breakdown of chitovibrin by endogenous protease activity of *Vibrio parahemnolyticus;* said polypeptide has a molecular weight about 80–85 kDa as determined by sodium dodecyl sulfate-polyacrylamide gel electrophoresis; said polypeptide binds chitin at an optimum pH of about 6; said polypeptide binds to chitin in aqueous solutions throughout a range of NaCl concentrations from 0 M NaCl to about 4 M NaCl; wherein chitovibrin is a larger protein of molecular weight about 134 kDa as determined by sodium dodecyl sulfate-polyacrylamide gel electrophoresis; wherein chitovibrin has affinity for chitin and for chitooligomers dp9 and larger; wherein chitovibrin is obtained from or is identical to a protein obtained from secretions from marine bacteria of the genus Vibrio induced by the presence of chitin, chitin oligomers, or cellobiose; wherein chitovibrin has an isoelectric pH of about 3.6; wherein chitovibrin binds chitin at an optimum pH of about 6; wherein chitovibrin binds to chitin in aqueous solutions throughout a range of NaCl concentrations from 0 M NaCl to about 4 M NaCl; and wherein chitovibrin has no hydrolytic activity towards chitin, towards chitin oligomers, or towards chitobiose.

* * * * *